(12) United States Patent
Ford et al.

(10) Patent No.: US 6,365,739 B1
(45) Date of Patent: Apr. 2, 2002

(54) PROCESS FOR THE PREPARATION OF 4,6-DISUBSTITUTED 2-ISOCYANATOPYRIMIDINES AND THEIR USE AS INTERMEDIATES FOR ACTIVE COMPOUND SYNTHESES

(75) Inventors: Mark James Ford, Bad Soden; Stephen Lachhein, Hofheim-Wallau, both of (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/358,297

(22) Filed: Jul. 21, 1999

(30) Foreign Application Priority Data

Jul. 23, 1998 (DE) .......................... 198 33 007

(51) Int. Cl.$^7$ ................. C07D 239/42; C07D 239/46; C07D 239/50
(52) U.S. Cl. ............... 544/320; 544/321; 544/330; 544/331; 544/182
(58) Field of Search ............... 544/320, 321, 544/182, 330, 331

(56) References Cited

U.S. PATENT DOCUMENTS

| | | | |
|---|---|---|---|
| 4,822,402 A | * | 4/1989 | Kimura et al. ............ 544/320 |
| 5,612,286 A | | 3/1997 | Mayer et al. ............ 544/321 |

FOREIGN PATENT DOCUMENTS

| | | | |
|---|---|---|---|
| BR | 8602648 | | 6/1986 |
| DE | 42 06 145 | | 9/1993 |
| DE | 43 22 726 | | 1/1995 |
| EP | 0232067 | * | 8/1987 |

OTHER PUBLICATIONS

Galletti et al., Collection of Ion–Trap Mass Spectra of Sulfonyurea Pyrolysis Products, Journal of Mass Spectrometry, vol. 30, pp. 333–338, 1995.

J.P. Senet, Societe Nationale des Pondres et Explosives (ed.), "The Recent Advance in Phosgene Chemistry", (1997), pp. 105–106.

* cited by examiner

*Primary Examiner*—Richard L. Raymond
*Assistant Examiner*—Venkataraman Balasubramanian
(74) *Attorney, Agent, or Firm*—Frommer Lawrence & Haug LLP

(57) ABSTRACT

Isocyanates of the formula (I)

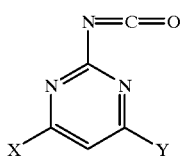

(I)

in which X and Y are defined as in formula (I) of claim 1 can be prepared by reacting a compound of the formula (II) or its salts

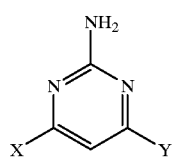

(II)

in which X and Y are defined as in formula (I), with 1 to 6 mol of phosgene per mole of compound of the formula (II), in the presence of 2 to 3.5 molar equivalents of a base per mole of compound of the formula (II) and in the presence of an aprotic organic solvent at a reaction temperature in the range from −30 to +60° C. to give the compound of the formula (I). The compounds (I) can be converted by reaction with nucleophiles to give addition products, such as carbamates, ureas and sulfonylureas and corresponding products, e.g. herbicidal sulfonylureas.

16 Claims, No Drawings

PROCESS FOR THE PREPARATION OF 4,6-DISUBSTITUTED 2-ISOCYANATOPYRIMIDINES AND THEIR USE AS INTERMEDIATES FOR ACTIVE COMPOUND SYNTHESES

DESCRIPTION

Process for the preparation of 4,6-disubstituted 2-isocyanatopyrimidines and their use as intermediates for active compound syntheses.

The invention relates to the technical field of the chemical synthesis of biologically active compounds, preferably the processes for the preparation of plant protection agents and of intermediates for these processes.

It is known that 4,6-disubstituted 2-isocyanatopyrimidines can be employed in principle as intermediates for the production of pharmaceuticals, plant protection agents, polymers or dyes from the chemical classes of the carbamates, ureas and sulfonylureas; cf. e.g. EP-A-232067, BR-A8602648 and chemical handbooks. Only a few processes are published for the preparation of the reactive isocyanate group on the pyrimidine radical.

According to J. Mass Spec. 30 (1995) p. 338, 4,6-dimethoxy-2-isocyanato-pyrimidine was produced in the high temperature pyrolysis (400–900° C.) of certain sulfonylurea derivatives and characterized by mass spectroscopy. The pyrolysis process, however, has only minor industrial importance, because the product cannot be obtained therewith in appreciable preparative amounts.

EP-A-232067 describes the phosgenation of 2-amino-4, 6-dimethoxy-pyrimidine in the presence of an amine base (triethylamine), where the intermediate, however, has not been isolated or characterized, but has been directly further processed with a sulfonamide to give a sulfonylurea. According to a general scheme, 4,6-dimethoxy-2-isocyanatopyrimidine and/or N-(4,6-dimethoxypyrimidin-2-yl)carbamoyl chloride is postulated as an intermediate in EP-A-232067. The process for the preparation of the intermediate and the overall process to the herbicidal sulfonylurea, however, has some disadvantages, which stand against its implementation on the industrial scale. Firstly, a large excess of amine base (especially 4 equivalents of triethylamine) and a large excess of phosgene (especially 8 equivalents) are employed. Such an excess cannot be used on the industrial scale for reasons of process safety, product quality and reasons of cost. The product quality is particularly adversely affected, because under the conditions of the reaction and on distilling off the excess phosgene, which is carried out at 90° C. according to EP-A-232067, the base triethylamine and phosgene can react with one another (cf. also J.-P-Senet, "The Recent Advance in Phosgene Chemistry", Société des Poudres et Explosives (Ed.) 1997, pp. 105–106). This leads on the one hand, depending on the secondary reactions which are difficult to control in detail from reaction batch to reaction batch, to poorly reproducible reaction courses and yields and partly to toxicologically harmful by-products. In the known process, decomposition products and salts are produced which contribute to the increased contamination of the product. Moreover, the triethylamine can react with the phosgene in the gas phase during the reaction as a result of its relatively high vapor pressure and form a white precipitate at various sites of the apparatus used for the reaction and thus make the conduct of the reaction difficult and further impair the purity of the product.

Many isocyanates are very reactive and are therefore not isolated as a rule from the reaction mixture or a prepurified solution after the preparation, but further processed directly with nucleophilic compounds to give addition products. For the further processing of isocyanates of the abovementioned type, solvents or solvent mixtures are suitable to a differing extent. For example, the solvent mixture employed in EP-A-232067 for the further processing of the intermediate can only be separated off with difficulty after the reaction and can therefore not be used on the industrial scale. Because of the mentioned disadvantages of the known process, its yield for the preparation of the intermediate and its total yield for the preparation of the further processing products are not acceptable.

It was therefore the object to make available a modified process which in comparison with the abovementioned process represents an improved or industrially realizable preparation of 4,6-disubstituted 2-isocyanatopyrimidines and preferably also allows a further processing to give carbamates, ureas and sulfonylureas with advantages such as improved total yield and/or product purity, decreased use of starting materials or a simplified process course.

One subject of the invention is a process for the preparation of compounds of the formula (I)

(I)

in which each of the radicals X and Y independently of one another is hydrogen, halogen, $(C_1-C_4)$alkyl, $(C_1-C_4)$alkoxy or $(C_1-C_4)$alkylthio, where each of the last-mentioned 3 radicals is unsubstituted or substituted by one or more radicals from the group consisting of halogen, $(C_1-C_4)$alkoxy and $(C_1-C_4)$alkylthio, or di[$(C_1-C_4)$alkyl]amino, $(C_3-C_6)$cycloalkyl, $(C_3-C_5)$alkenyl, $(C_3-C_5)$alkynyl, $(C_3-C_5)$alkenyloxy or $(C_3-C_5)$alkynyloxy, which comprises reacting a compound of the formula (II) or its salts

(II)

in which X and Y are defined as in formula (I), with 1 to 6 mol of phosgene per mole of compound of the formula (II), in the presence of 2 to 3.5 molar equivalents of a base per mole of compound of the formula (II) and in the presence of an aprotic organic solvent at a reaction temperature in the range from −30 to +60° C., preferably in the range from −30 to +40° C., in particular in the range from −10 to +30° C., to give the compound of the formula (I).

Preferred processes for the preparation of compounds of the formula (I) are those in which each of the radicals X and Y independently of one another is hydrogen, halogen, methyl, ethyl, methoxy, ethoxy, methylthio, trifluoromethyl, trichloromethyl, difluoromethoxy, dimethylamino, diethylamino, allyl, propargyl, allyloxy or propargyloxy;

particularly preferred in this case are those processes in which one of the radicals X and Y is halogen, preferably chlorine, methyl, ethyl, methoxy, ethoxy, methylthio, trifluoromethyl, trichloromethyl, difluoromethoxy, dimethylamino, diethylamino, allyl, propargyl, allyloxy or propargyloxy and the other of the radicals X and Y is methyl, ethyl, methoxy, ethoxy, methylthio or difluoromethoxy;

very particularly preferred processes are those in which X and Y in pairs are methyl/methyl, methyl/methoxy, chlorine/methyl, chlorine/methoxy or methoxy/methoxy.

In connection with the chemical terms used in this description, the definitions customary for the person skilled in the art apply, if not specifically defined otherwise. The radicals alkyl, alkoxy, haloalkyl, haloalkoxy, alkylamino and alkylthio and the corresponding unsaturated and/or substituted radicals in the carbon structure are in each case straight-chain or branched. If not specially indicated, in these radicals the lower carbon structures, e.g. having 1 to 6 carbon atoms or in the case of unsaturated groups having 2 to 6 carbon atoms, are preferred.

Alkyl radicals, also in the combined meanings such as alkoxy, haloalkyl etc. are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meaning of the possible unsaturated radicals corresponding to the alkyl radicals; alkeryl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Cycloalkyl is a carbocyclic, saturated ring system preferably having 3–8 carbon atoms, e.g. cyclopropyl, cyclobutyl, cyclopentyl or cyclohexyl.

Halogen is, for example, fluorine, chlorine, bromine or iodine. Haloalkyl, -alkenyl and -alkynyl are alkyl, alkenyl or alkynyl which is partly or completely substituted by halogen, preferably by fluorine, chlorine and/or bromine, in particular by fluorine and/or chlorine, e.g. monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies to haloalkenyl and other radicals substituted by halogen.

Aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or heteroaromatic; it preferably contains one or more, in particular 1, 2 or 3, heteroatoms in the heterocyclic ring, preferably from the group consisting of N, O and S; it is preferably an aliphatic heterocyclyl radical having 3 to 7 ring atoms or a heteroaromatic radical having 5 or 6 ring atoms. The heterocyclic radical can be, for example, a heteroaromatic radical or ring (heteroaryl), such as, for example, a mono-, bi- or polycyclic aromatic system in which at least 1 ring contains one or more heteroatoms, for example pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl and imidazolyl, or is a partially or completely hydrogenated radical such as oxiranyl, pyrrolidyl, piperidyl, piperazinyl, dioxolanyl, oxazolinyl, isoxazolinyl, oxazolidinyl, isoxazolidinyl, morpholinyl, tetrahydrofuryl. Suitable substituents for a substituted heterocyclic radical are the substituents mentioned below, and additionally also oxo.

The oxo group can also occur on the heterocyclic ring atoms, which can exist in various oxidation states, e.g. in the case of N and S.

Substituted radicals, such as a substituted alkyl, alkenyl, alkynyl, aryl, phenyl, benzyl, heterocyclyl or heteroaryl radical, are, for example, a substituted radical derived from an unsubstituted parent structure, the substituents, for example, being one or more, preferably 1, 2 or 3, radicals from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, sulfamoyl, mono- and dialkylaminosulfonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl; in the expression "substituted radicals" such as substituted alkyl etc. corresponding unsaturated aliphatic and aromatic radicals, such as optionally substituted alkenyl, alkynyl, alkenyloxy, alkynyloxy, phenyl, phenoxy etc. are included as substituents additionally to the saturated hydrocarbon-containing radicals mentioned. In the case of radicals having carbon atoms, those having 1 to 4 carbon atoms, in particular 1 or 2 carbon atoms, are preferred. As a rule, preferred substituents are those from the group consisting of halogen, e.g. fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$ haloalkoxy, nitro and cyano. The substituents methyl, methoxy and chlorine are particularly preferred here.

All stereoisomers are also included by the formulae (I) and (II) and also the formulae for the secondary products (see below). Such compounds contain one or more asymmetric carbon atoms or alternatively double bonds which are not separately indicated in the formulae. The possible stereoisomers defined by their specific spatial shape, such as enantiomers, diastereomers, Z and E isomers can be obtained from mixtures of these stereoisomers by customary methods or alternatively prepared by stereoselective reactions in combination with the use of stereochemically pure starting substances.

The compounds of the formula (II) to be employed according to the invention and their salts are known or can be prepared analogously to generally known processes (cf. references to precursors for the preparation of herbicidal sulfonylureas).

In the reaction according to the invention of phosgene with the amine compound of the formula (II), according to the stoichiometry of the reaction 2 mol of HCl, which should be bound by the base, are set free per mole of reacted phosgene. Possible bases are basic compounds which do not react or essentially do not react with the isocyanate of the formula (I) under the reaction conditions of the process according to the invention. Suitable bases are especially organic amine bases, such as primary, secondary and tertiary amines, in particular sterically hindered secondary or, preferably, tertiary amines.

Suitable bases are from the group consisting of the mono-, di- and trialkylamines, mono-, di- and triarylamines, N-alkyl-N-arylamines, N,N-dialkyl-N-arylamines and N-alkyl-N,N-diarylamines, each of the last-mentioned 9 amines independently of one another having 1 to 12 carbon atoms, preferably 1 to 6 carbon atoms, in particular 1 to 4 carbon atoms, in each alkyl moiety and each of the amines mentioned independently of one another being unsubstituted or further substituted with suitable aprotic radicals on the alkyl moieties or aryl moieties.

Suitable amine bases are also amines having several amino groups, which preferably contain secondary or, in particular, tertiary amino groups.

Examples of amines which can be employed are trialkylamines or dialkylanilines such as trimethylamine, triethylamine, preferably N,N-dimethylaniline, N,N-diisopropyl-N-ethylamine or tributylamine.

The base used can also partly or completely be the compound of the formula (II). In this case, the quantitative ratios of phosgene to the compound of the formula (II) are, according to the invention, in the range from 0.33 to 2 mol of phosgene per mole of compound of the formula (II), preferably 0.33 to 1 mol of phosgene, in particular 0.33 to 0.66 mol of phosgene per mole of compound of the formula (II).

As a rule, the process according to the invention is carried out such that the compound of the formula (II), preferably 4,6-dimethoxy-2-isocyanato-pyrimidine, dissolved in a largely anhydrous, preferably anhydrous, aprotic organic solvent is reacted with phosgene using 2 to 3.5 molar equivalents, preferably 2 to 3 molar equivalents, in particular 2 to 2.2 molar equivalents, in each case relative to 1 mol of compound of the formula (II) to be reacted, 1 to 6, preferably 1 to 4, in particular 1 to 3, very particularly 1.5 to 2, molar equivalents of phosgene being employed per mole of compound of the formula (II) to be reacted. As a rule, the isocyanate of the formula (I) produced can be characterized, e.g. (10% solution in dioxane: IR 2240 cm$^{-1}$).

Possible solvents are aprotic organic solvents which are inert under the reaction conditions, for example

- aliphatic and aromatic hydrocarbons, such as, for example, mineral oils, petroleum ether, cyclohexane or toluene, xylenes, naphthalene derivatives, ®Solvesso 200 (high-boiling aromatic mixture);
- halogenated aliphatic and aromatic hydrocarbons, such as methylene chloride, dichloroethane, chloroform or chlorobenzene;
- cyclic or open-chain ethers, such as diethyl ether, di-n-propyl ether, diisopropyl ether, methyl tert-butyl ether, tetrahydrofuran (THF), dioxane, alkylene glycol dialkyl ethers such as, for example, propylene glycol dimethyl ether, propylene glycol diethyl ether, ethylene glycol dimethyl ether or diethyl ether, dimethoxyethane, diglyme, triglyme and tetraglyme;
- sulfones such as sulfolane,
- carboxylic acid esters, such as the esters of mono-, di- and tricarboxylic acids preferably having 1 to 4 carbon atoms and aliphatic (including cycloaliphatic) alcohols having 1 to 10 carbon atoms, for example ethyl formate, methyl acetate, ethyl acetate, n-propyl acetate, i-propyl acetate, esters of acetic acid with n-, i-, sec- or tert-butanol,
- esters of carbonic acid with aliphatic (including cycloaliphatic) alcohols having 1 to 10 carbon atoms, for example diethyl carbonate,
- mixtures of several of the abovementioned solvents.

The reaction according to the invention is carried out, for example, such that phosgene is passed into a solution or suspension of the compound of the formula (II) in the organic solvent, preferably at a temperature below +40° C., in particular below +30° C. The base, preferably an amine base in pure form or in the form of a solution, can then be added dropwise to the organic solvent or a solvent of the same type at the same temperature. Alternatively, phosgene can be introduced into an organic solvent and the compound of the formula (II) and the base can be added successively or together, in pure form or preferably in the form of a solution in the organic solvent, at a comparable temperature.

If a compound of the formula (II) such as 2-amino4,6-dimethoxypyrimidine is also utilized for the reaction as a base, preferably 0.33 to 1 molar equivalent of phosgene, in particular 0.6 to 0.7 molar equivalent of phosgene, is employed relative to the total amount of compound (II). The stoichiometric yield in this process variant is 0.33 molar equivalent of compound (I) and 0.66 molar equivalent of HCl salt of the compound of the formula (II), in each case relative to compound (II) employed. As a rule, the salt of the compound (II) can be filtered off and the solution of the isocyanate can be further used and the compound of the formula (II) can be recovered as the free base from the salt by treatment with a strong base, e.g. aqueous solutions of alkali metal hydroxides such as sodium hydroxide solution.

An excess of phosgene which may be employed can be removed after the reaction, for example, by blowing through nitrogen, e.g. at 10 to 30° C., or by distillation under vacuum (bottom temperature preferably below 40° C.). The salts formed, as a rule the amine hydrochloride salts, can be filtered off, for example, before or after the removal of the phosgene. The solution of the compound of the formula (I) can then be employed directly for subsequent reactions. Alternatively, the reaction mixture can also be further employed directly as a suspension or as a.,solution without desalting after removal of the phosgene.

The preparation of isocyanates of the formula (I) described above is surprisingly very highly reproducible, as a rule gives a good to excellent yield, makes possible a reduction of the need for phosgene and amine base in comparison to the known process from EP-A-232067 with functionally identical or similar intermediates and can be carried out on the industrial scale.

The compounds of the formula (I) obtained according to the invention in dissolved form can expediently be reacted in a manner known per se with nucleophiles, preferably protic nucleophiles, to give derivatives of very different types. For example, reaction with alcohols makes possible the preparation of carbamates, reaction with primary or secondary amines affords ureas and reaction with sulfonamides affords sulfonylureas.

The invention therefore also relates to the use of the compounds of the formula (I) obtained according to the invention for the preparation of further processing products and corresponding processes. The further processing products preferably contain a substructure of the compound (I), for example the substructure of the formula

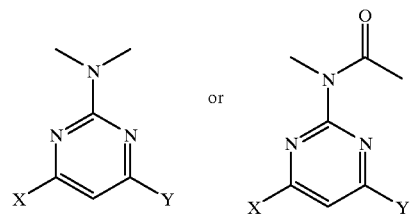

(Comment: The free bonds marked should not be methyl groups, but the bonding sites of the substructure).

Particularly preferred processes here are those for the preparation of compounds of the formula (III)

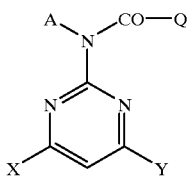

(III)

in which X and Y are as defined in formula (I) and A and Q have the meanings mentioned below, which comprise preparing, according to the invention, an isocyanate of the formula (I) and then reacting it in a manner known per se with nucleophiles of the formula (IV)

A—Q    (IV)

in which

A is hydrogen or a functionally comparable group and
Q is the radical of a nucleophile, at the isocyanate group to give the further processing products (III).

The moiety Q contains the nucleophilic group which bonds to the electrophilic carbon atom of the isocyanate group. In protic nucleophiles, A=hydrogen; in nonprotic nucleophiles A is other than hydrogen, for example A=a cation, e.g. an alkali metal cation such as a sodium or potassium cation.

Suitable nucleophiles are, for example, the following nucleophiles:

Compounds of the formula (IV), in which A=H or a cation and Q is a radical of the formula R*—Z—, in which Z is a divalent group of the formula —O—, —S—, —NR—, —CO—NR—, —CS—NR—, —SO$_2$—, —SO$_2$—NR—, —SO— or —SO$_2$—NR—SO$_2$—, in which R is in each case H or one of the radicals defined for R*, preferably H or alkyl, alkenyl, alkynyl, cycloalkyl, cycloalkenyl or alkoxy, particularly preferably H or alkyl having 1 to 6 carbon atoms, in particular methyl or ethyl, and R* is a radical from the group consisting of alkyl, alkenyl, alkynyl, cycloalkyl, cycloalkenyl, alkoxy, aryl or heteroaryl, where each of the last-mentioned 8 radicals is unsubstituted or substituted, preferably is unsubstituted or substituted, by one or more aprotic radicals, in particular is unsubstituted or substituted, by radicals from the group consisting of halogen, alkyl, haloalkyl, alkoxy, haloalkoxy, alkylthio, nitro, cyano, azido, alkoxycarbonyl, alkylcarbonyl, formyl, mono- and dialkylaminocarbonyl, mono- and dialkylaminosulfonyl, substituted amino, such as acylamino, mono- and dialkylamino, alkylsulfinyl, haloalkylsulfinyl, alkylsulfonyl and haloalkylsulfonyl.

Preferred compounds of the formula (IV) are the
sulfonamides of the formula $R^1$—SO$_2$—NH$_2$
sulfonamides of the formula $R^1$—SO$_2$—NR—SO$_2$—NH$_2$
sulfonamides of the formula $R^1$—NR—SO$_2$—NH$_2$
sulfonamides of the formula $R^1$—O—SO$_2$—NH$_2$
alcohols of the formula $R^2$—OH
amines of the formula $R^3$—NH—R'
(=formula (IV), in which A=H, Q=$R^1$—SO$_2$—NH—, $R^1$—SO$_2$—NR—SO$_2$—NH—, $R^1$—NR—SO$_2$—NH—, $R^2$—O— or $R^3$—NR'—)
in which
each of the radicals $R^1$, $R^2$ and $R^3$ independently of one another is a radical from the group consisting of alkyl, alkenyl, alkynyl, cycloalkyl, alkoxy, cycloalkenyl, aryl or heteroaryl, where each of the last-mentioned 8 radicals is unsubstituted or substituted, preferably is unsubstituted or substituted, by one or more aprotic radicals, and each of the radicals R and R' independently of one another is a radical such as the radicals possible for $R^1$, $R^2$ or $R^3$ or H, preferably H or alkyl having 1 to 6 carbon atoms.

Preferably, $R^1$ is a radical of sulfonamides which are suitable for the preparation of biologically active sulfonylureas, preferably sulfonylurea herbicides.

Particularly preferred compounds (IV) are the sulfonamides of the formula $R^1$—SO$_2$—NH$_2$ or $R^1$—NR—SO$_2$—NH$_2$, in which $R^1$ is phenyl or heteroaryl, where each of the two last-mentioned radicals is unsubstituted or preferably substituted by one or more aprotic radicals, preferably from the group consisting of halogen, alkyl, haloalkyl, alkoxy, haloalkoxy, alkylthio, nitro, cyano, azido, alkoxycarbonyl, alkylcarbonyl, formyl, mono- and dialkylaminocarbonyl, mono- and dialkylaminosulfonyl, substituted amino, such as acylamino, e.g. acetylamino, mono- and dialkylamino, alkylsulfinyl, haloalkylsulfinyl, alkylsulfonyl and haloalkylsulfonyl, and R is H or ($C_1$–$C_4$)alkyl.

Particularly preferred sulfonamides are also those of the formula $R^1$—SO$_2$—NR—SO$_2$—NH$_2$, in which $R^1$ is alkyl which is unsubstituted or substituted by one or more aprotic radicals from the group consisting of halogen, alkyl, haloalkyl, alkoxy, haloalkoxy, alkylthio and phenyl, which is unsubstituted or substituted, e.g. as explained above for $R^1$=phenyl and heteroaryl, in particular $R^1$=($C_1$–$C_4$)alkyl, and R is H or ($C_1$–$C_4$)alkyl.

Appropriate radicals are preferred, such as can be employed in sulfonamides for the preparation of known herbicidal sulfonylureas or hitherto still unknown compounds of the same structural class and trend of action (cf. "The Pesticide Manual", 11th Edition, 1997, British Crop Protection Council and references' cited therein).

Preferably, $R^2$ is a radical such as is generally defined for $R^1$, in particular alkyl, cycloalkyl or phenyl, each of the last-mentioned 3 radicals being unsubstituted or substituted by one or more aprotic radicals. Examples of compounds of the formula $R^2$OH are alkanols, phenol or substituted phenols. Preferably, $R^3$ is a radical such as is defined for $R^1$, in particular alkyl, cycloalkyl or phenyl, each of the last-mentioned 3 radicals being unsubstituted or substituted by one or more aprotic radicals, and R' independently of one another is a radical such as the radicals possible for R or H, preferably H or alkyl having 1 to 6 carbon atoms.

As a rule, the preparation of the compounds of the formula (III) is carried out such that the compounds (I) are reacted in the presence of a small excess of a nucleophile, for example of an alcohol or primary amine, in an organic solvent, preferably in the organic solvent used in the preparation of the compound (I), if appropriate with addition of a base as a catalyst or for the satisfaction of the product. Possible bases here are not only amino bases, but also other bases, for example metal alkoxides, such as alkali metal alkoxides.

The further processing reaction is preferably carried out in the temperature range which is also suitable for the preparation of the compounds (I), for example in the range from −30 to +60° C., preferably in the range from −30 to +40° C., in particular in the range from −10 to +30° C.

For the preparation of a sulfonylurea, it is possible to add, for example, the sulfonamide of the formula (IV) to the solution of the isocyanate as a solid, liquid or in solution, and to add the base, e.g. a metal alkoxide or an amine base, in pure form or in solution, dropwise at this temperature, or else the isocyanate in solution or suspension can be added dropwise to a mixture of sulfonamide (IV) and of an amine base or a salt of the sulfonamide, for example the sodium or potassium salt.

The carbamates, ureas and sulfonylureas prepared in this way can be isolated and purified by methods which are customary in laboratory and process technology, e.g. by filtration or extraction.

In a preferred variant of the process according to the invention the same organic solvent, preferably one of the preferred organic solvents mentioned for the process for the preparation of the compound (I), is used both in the stage of the preparation of the compound (I) and in the further processing of the isocyanate. An advantage of the process according to the invention is that a simple procedure is possible and that the working-up surprisingly proceeds with particularly good yields.

Optionally, the preparation of the further processing products may also require a number of chemical or physical process stages.

The following examples explain the process according to the invention in greater detail without restricting the process according to the invention thereto. In the following examples, quantitative data relate to the weight, if not specifically defined otherwise. Customary abbreviations are used for mass units and physical parameters, for example h=hour(s), m.p.=melting point, l=liter, g=gram, min=minute (s), in vac.="in vacuo"=under reduced pressure.

EXAMPLES

1) Isopropyl N-(4,6-Dimethoxypyrimidin-2-yl) carbamate

Phosgene (20 g, 202 mmol) was passed at 20–25° C. in the course of 45 min into a recipient vessel of ethyl acetate (120 ml). A solution of 2-amino4,6-dimethoxypyrimidine (15.6 g, 101 mmol) and N,N-dimethyl-aniline (26 ml, 203 mmol) in ethyl acetate (90 ml) was added dropwise at 25° C. in the course of 3 h. After 15 min, the suspension was aerated with nitrogen until it was free of phosgene, ethyl acetate (120 ml) was added and isopropanol (10 ml, 130 mmol) was added dropwise in the course of 10 min with cooling (20–25° C.). The reaction was filtered after 1 h, washed with ethyl acetate (3×20 ml) and the combined filtrates were extracted with hydrochloric acid (1.0 N, 2×30 ml) and water (2×30 ml). The solution was then concentrated and the product was crystallized from the residue; yield 19.2 g (80% of theory), m.p. 51–54° C.

2) Phenyl N-(4,6-Dimethoxypyrimidin-2-yl) carbamate

The procedure was analogous to Example 1, but instead of isopropanol a solution of phenol (10.3 g, 110 mmol) in ethyl acetate was added dropwise. Phenyl N-(4,6-dimethoxypyrimidin-2-yl)carbamate was obtained in a yield of 82% of theory.

3) N'-(4,6-Dimethoxypyrimidin-2-yl)-N-(2-ethoxyphenoxysulfonyl)urea

Ethyl acetate (16 ml) was introduced and cooled to −10° C. under nitrogen. Phosgene (4.0 g, 0.04 mol) was passed in at this temperature and then a solution of 2-amino-4,6dimethoxypyrimidine (2.86 g, 0.0185 mol) and triethylamine (3.73 g, 0.037 mol) in ethyl acetate (20 ml) was added dropwise in the course of 2 h. After 1 h, the reaction was warmed to 20° C., nitrogen was blown through until there was no longer phosgene in the solution, and then a solution of 2-ethoxyphenoxysulfonamide (4.0 g, 0.0184 mol) in ethyl acetate (10 ml) and triethylamine (1.86 g, 0.0184 mol) in ethyl acetate (10 ml) were successively added dropwise in the course of 30 min. After 30 min, water (100 ml) was added, the phases were separated and the organic phase was extracted with 2×25 ml of 1.5M sodium hydroxide solution. The aqueous phases were combined, washed with xylene (20 ml), adjusted to pH=2 using 6M hydrochloric acid and the product was filtered off and dried; yield: 5.57 g, 70.7% of theory.

4) N,N-Dimethyl-2-{N-[N-(4,6-dimethoxypyrimidin-2-yl)aminocarbonyl]aminosulfonyl}-4-nitrobenzamide Ethyl acetate (16 ml) and 2-amino-4,6-dimethoxypyrimidine (5.0 g, 32.2 mmol) were introduced and cooled to −10° C. under nitrogen. Phosgene (5.1 g, 51.5 mmol) was passed in at this temperature and a solution of triethylamine (6.5 g, 64.2 mmol) in ethyl acetate (20 ml) was added dropwise in the course of 1 hour. After 1 hour, the reaction was warmed to 20° C. and nitrogen was blown through until it no longer contained phosgene, and then N,N-dimethyl-2-aminosulfonyl-4-nitrobenzamide (8.1 g, 29.6 mmol) was added. The mixture was cooled to −10° C. and a solution of triethylamine (3.3 g, 32.7 mmol) in ethyl acetate (15 ml) was added dropwise in the course of 60 minutes, and the mixture was stirred for 30 minutes and warmed to room temperature. Potassium hydroxide solution (1.0M, 100 ml) was then added, the phases were separated and the aqueous phase was extracted with ethyl acetate. The aqueous phase was adjusted to pH=2 using 6M hydrochloric acid, and the product was filtered off, washed with water (2×20 ml) and dried. Yield: 10.28 g, 72.6% of theory.

5) Methyl 2-{N-[N-4,6-Dimethoxypyrimidin-2-yl) aminocarbonyl]aminosulfonyl}-4-cyanobenzoate The procedure was analogous to Example 4, but instead of N,N-dimethyl-2-aminosulfonyl-4-nitrobenzamide, methyl 2-aminosulfonyl-4-cyanobenzoate (7.1 g, 29.6 mmol) was employed. Methyl 2-{N-(4,6-dimethoxypyrimidin-2-yl)aminocarbonyl]aminosulfonyl}-4-cyanobenzoate was obtained in a yield of 71% of theory.

6) N,N-Dimethyl-2-{N-[N-(4,6-dimethoxypyrimidin-2-yl)aminocarbonyl]aminosulfonyl}-nitrobenzamide Phosgene (23 g, 232 mmol) was passed into ethyl acetate (250 ml) at 10° C. A solution of 2-amino-4,6-dimethoxypyrimidine (20 g, 129 mmol) and tributylamine (47.82 g, 258 mmol) in ethyl acetate (270 ml) was added dropwise in the course of 3 h. 15 min after the addition, the jacket was warmed to 30° C. and ethyl acetate and excess phosgene were distilled off in vac. The remaining solution of the isocyanate was cooled to 10° C. and added dropwise to a suspension of N,N-dimethyl-2-aminosulfonyl-4-nitro-benzamide (31.7 g, 116 mmol) and tributylamine (22.96 g, 232 mmol) in ethyl acetate (100 ml) at 20° C. in the course of 3 h. The mixture was stirred for 1 h and treated with water (300 ml) and potassium hydroxide solution (10% strength, 240 ml). After phase separation, the organic phase was extracted with water (50 ml). The combined aqueous phases were extracted with ethyl acetate (50 ml) and adjusted to pH 2 to 3 using 6M hydrochloric acid. After filtering off the product, washing with water (2×100 ml) and drying, 49.09 g (85.8% of theory) of N,N-dimethyl-2{-N-[N-(4,6-dimethoxypyrimidin-2-yl)aminocarbonyl]aminosulfonyl}-4-nitrobenz-amide were obtained.

COMPARISON EXAMPLE

Preparation of a Sulfonylurea Analogously to the Procedure of EP-A-232067

A solution of 2-amino-4,6-dimethoxypyrimidine (9.3 g, 60 mmol) and triethylamine (24.28 g, 240 mmol) in ethyl acetate (100 ml) was added dropwise to a solution of phosgene (47.11 g, 476 mmol) in ethyl acetate (196.3 ml) at 15° C. in the course of 40 minutes. Stirring was carried out for 1 hour. The mixture was heated to 90° C. and the excess phosgene was distilled off using ethyl acetate. The batch was cooled to room temperature and a solution of 2-aminosulfonyl4-nitro-N,N-dimethylbenzamide (20.3 g, 74.3 mmol) in acetonitrile (350 ml) was added dropwise in the course of 30 minutes. Triethylamine (7.2 g, 71.1 mmol) was then added dropwise in the course of 1 hour and the batch was stirred for 1.5 hours. The mixture was then poured into water (300 ml), the phases were separated and the aqueous phase was adjusted to pH=2 using hydrochloric acid (18.5% strength) (30 ml), and the product was filtered off, washed with water (2×20 ml) and dried. Yield: 21.7 g, 54% of theory.

What is claimed is:

1. A process for the preparation of compounds of the formula (I)

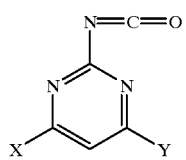
(I)

in which each of the radicals X and Y independently of one another is hydrogen, halogen, $(C_1-C_4)$alkyl, $(C_1-C_4)$alkoxy or $(C_1-C_4)$alkylthio, where each of the last-mentioned 3 radicals is unsubstituted or substituted by one or more radicals from the group consisting of halogen, $(C_1-C_4)$alkoxy and $(C_1-C_4)$-alkylthio, or di[$(C_1-C_4)$alkyl]amino, $(C_3-C_6)$cycloalkyl, $(C_3-C_5)$-alkenyl, $(C_3-C_5)$alkynyl, $(C_3-C_5)$alkenyloxy or $(C_3-C_5)$-alkynyloxy, which comprises reacting a compound of the formula (II) or its salts

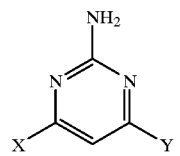
(II)

in which X and Y are defined as in formula (I), with 1 to 6 mol of phosgene per mole of compound of the formula (II), in the presence of 2 to 3.5 molar equivalents of a base per mole of compound of the formula (II) and in the presence of an aprotic organic solvent at a reaction temperature in the range from −30 to +60° C., to give the compound of the formula (I).

2. The process as claimed in claim 1, wherein X and Y in pairs are methyl/methyl, methyl/methoxy, chlorine/methyl, chlorine/methoxy or methoxy/methoxy.

3. The process as claimed in claim 1, wherein the reaction is carried out in the presence of 2 to 3 molar equivalents of base, relative to 1 mol of compound of the formula (II) to be reacted.

4. The process as claimed in claim 1, wherein an organic amine base is employed as a base.

5. The process as claimed in claim 1, wherein the compound of the formula (II) is also employed as a base.

6. The process as claimed in claim 1, wherein 1 to 3 molar equivalents of phosgene are employed per mole of compound of the formula (II) to be reacted.

7. The process as claimed in claim 6, wherein 1.5 to 2 molar equivalents of phosgene are employed per mole of compound of the formula (II) to be reacted.

8. The process as claimed in claim 1, wherein a solvent from the group consisting of aliphatic and aromatic hydrocarbons, halogenated aliphatic and aromatic hydrocarbons, cyclic or open-chain ethers, sulfones, carboxylic acid esters, esters of carbonic acid with and mixtures of several of the abovementioned solvents is employed.

9. The process as claimed in claim 8, wherein an ester of mono-, di- and tricarboxylic acids having 1 to 4 carbon atoms and aliphatic alcohols having 1 to 10 carbon atoms is employed as a solvent.

10. A process for the preparation of products derived from compounds of formula (I) which comprises:

preparing the compounds of formula (I)

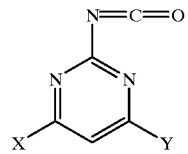
(I)

in which each of the radicals X and Y independently of one another is hydrogen, halogen, $(C_1-C_4)$alkyl, $(C_1-C_4)$ alkoxy or $(C_1-C_4)$alkylthio, where each of the last-mentioned 3 radicals is unsubstituted or substituted by one or more radicals from the group consisting of halogen, $(C_1-C_4)$alkoxy and $(C_1-C_4)$alkylthio, or di[$(C_1-C_4)$alkyl]amino, $(C_3-C_6)$cycloalkyl, $(C_3-C_5)$ alkenyl, $(C_3-C_5)$alkynyl, $(C_3-C_5)$alkenyloxy or $(C_3-C_5)$alkynyloxy, by reacting a compound of the formula (II) or its salt

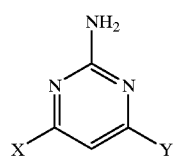
(II)

in which X and Y are as defined in formula (I), with 1 to 6 mol of phosgene per mole of compound of the formula (II), in the presence of 2 to 3.5 molar equivalents of a base per mole of compound of the formula (II) and in the presence of an aprotic organic solvent at a reaction temperature in the range from −30 to +60 ° C., to give the compound of the formula (I); and reacting the formula (I) compound obtained in one or more steps to produce said products.

11. The process as claimed in claim 10, wherein the compound of the formula (I) first obtained is reacted with nucleophiles of the formula (IV)
in which
A is hydrogen or a cation and
Q is a radical selected from the group of protic nucleophiles and aprotic nucleophiles at the isocyanate group to give compounds of the formula (III),

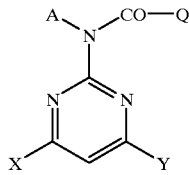

(III)

in which X and Y are as defined in formula (I) and A and Q are as defined in formula (IV).

12. The process as claimed in claim 11, wherein A is hydrogen or a cation, and

Q is a radical of the formula R*—Z—, in which
Z is a divalent group of the formula —O—, —S—, —NR—, —CO—NR—, —CS—NR—, —SO$_2$—, —SO$_2$—NR—, —SO— or —SO$_2$—NR—SO$_2$—, in which R is in each case H or one of the radicals defined for R*, and
R* is a radical from the group consisting of alkyl, alkenyl, alkynyl, cycloalkyl, cycloalkenyl, alkoxy, aryl or heteroaryl, where each of the last-mentioned 8 radicals is unsubstituted or substituted.

13. The process as claimed in claim 11, wherein the compounds of the formula (III) are from the carbamates, ureas or sulfonylureas group.

14. The process as claimed in claim 13 wherein the compounds of formula (III) are sulfonylureas.

15. In a process for preparing a carbamate, urea or sulfonylurea compound the improvement which comprises employing a compound of formula (I) according to claim 1 as an intermediate.

16. The process according to claim 15, wherein the compound is a pharmaceutical, plant protecting agent, polymer or dye.

* * * * *